United States Patent
Kasai et al.

(10) Patent No.: US 6,395,535 B1
(45) Date of Patent: May 28, 2002

(54) OPTICAL RESOLUTION OF 4-HALOGENO-3-ALKANOYLOXY-BUTYRONITRILE

(75) Inventors: Naoya Kasai, Sennan-gun; Toshio Suzuki, Amagasaki; Hideaki Idogaki, Amagasaki; Miki Hatada, Amagasaki; Motoko Takeuchi, Amagasaki, all of (JP)

(73) Assignee: Daiso Co., Ltd., Osaka (JP)

( * ) Notice: Subject to any disclaimer, the term of this patent is extended or adjusted under 35 U.S.C. 154(b) by 0 days.

(21) Appl. No.: 09/542,252

(22) Filed: Apr. 3, 2000

(30) Foreign Application Priority Data

Apr. 5, 1999 (JP) ............................... 11-097527

(51) Int. Cl.$^7$ ................................ C12P 41/00
(52) U.S. Cl. ..................................... 435/280
(58) Field of Search ........................... 435/280

(56) References Cited

FOREIGN PATENT DOCUMENTS

| EP | 0 745 681 | 12/1996 |
| JP | 02-027995 | * 1/1990 |
| JP | 05-219965 | 8/1993 |

OTHER PUBLICATIONS

Langrand et al., "Lipase Catalyzed Reactions and Strategy for Alcohol Resolution", Tetrahedron Letters 27 (1): 29–32 (1986).*
Nakamura, T. et al, "A New Catalytic Function Of Halohydrin Hydrogen–Halide–Lyase, Synthesis of β–Hydroxynitriles From Epoxides and Cyanide", Biochemical and Biophysical Research Communications, vol. 180, No. 1, Oct. 15, 1991, pp. 124–130.
Suzuki, T. et al, "Production of (S)–4–Chloro–3–Hydroxybutyro–nitrile Using Microbial Resolution", Bioorganic & Medicinal Chemistry Letters, vol. 6, No. 21, 1996, pp. 2581–2584.

* cited by examiner

Primary Examiner—Sandra E. Saucier
(74) Attorney, Agent, or Firm—Jacobson Holman, PLLC

(57) ABSTRACT

A process for preparation of optically active 4-halogeno-3-hydroxybutyronitrile and 4-halogeno-3-alkanoyloxybutyronitrile, which are simply and economically prepared by reacting a racemic 4-halogeno-3-alkanoyloxybutyronitrile with a microorganism such as a strain of the genus Pseudomonas or the genus Enterobacter, which has the activity stereoselectively hydrolyzing the ester portion, its culture broth or an enzyme(s) derived from the microorganism or an enzyme preparation such as a lipase preparation.

12 Claims, No Drawings

OPTICAL RESOLUTION OF 4-HALOGENO-3-ALKANOYLOXY-BUTYRONITRILE

TECHNICAL FIELD

4-Halogeno-3-hydroxybutyronitrile and its ester are very important as intermediates in making pharmaceuticals, agrochemicals, ferro electric liquid crystals and optically active polymers.

PRIOR ART

As to processes for preparation of 4-halogeno-3-hydoxybutyronitrile, there are known following processes: A method for preparing it by adding cyano group to epichlorohydrin chemically or enzymatically (Japanese Patent Publication A 5-219965; T. Nakamura et al. Biochem. Biophysic. Res. Commun., Vol. 180, No.1, 124–130 (1991)). A method for preparing it by reacting 4-chloro-3-hydoxybutyronitrile in racemate with a microorganism possessing stereoselectively dehalogenating activity to obtain optically active 4-chloro-3-hydroxybutyronitrile in residue (T. Suzuki et al.; Bioorg. & Med. Chem. Lett., Vol. 6, 2581–2584 (1996); European Patent Publication A 0745681 (1996)).

However, these known methods are not suitable for mass production and therefore, more simple and economical methods have been desired.

BRIEF DESCRIPTION OF THE INVENTION

As a result of extensive investigation, the present inventors have found that optically active compounds [2] and [3] mentioned below are simply and economically prepared by reacting a racemic compound [1] mentioned below with a microorganism which has the activity stereoselectively hydrolyzing the ester portion, its culture broth or an enzyme(s) derived from the microorganism or moreover, its enzyme preparation.

That is, the present invention relates to a process for preparation of optically active compounds [2] and [3] represented by following formulae

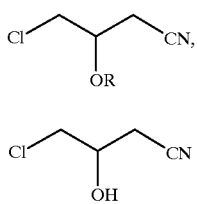

in which R means $C_2$–$C_4$ alkanoyl group,
which comprises reacting a racemic 4-halogeno-3-alkanoyloxybutyronitrile represented by following formula

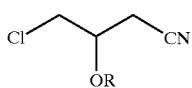

in which R is defined above,
with a microorganism which has the activity stereoselectively hydrolyzing the ester portion, its culture broth or an enzyme(s) derived from the microorganism to make it optical resolution.

The present invention more in detail, relates to a process for preparation of an optically active compound [2] in (S) form and an optically active compound [3] in (R) form by reacting a racemic compound [1] with a microorganism which has the activity stereoselectively hydrolyzing the ester portion of (R) form, its culture broth or an enzyme(s) derived from the microorganism, and to a process for preparation of an optically active compound [2] in (R) form and an optically active compound [3] in (S) form by reacting a racemic compound [1] with a microorganism which has the activity stereoselectively hydrolyzing the ester portion of (S) form, its culture broth or an enzyme(s) derived from the microorganism.

DETAILED DESCRIPTION OF THE INVENTION

The present invention is practiced in accordance with the following method.

Optically active compounds [2] and [3] from a racemic compound [1] are obtainable by reacting the substrate [1] with an enzyme(s) which has the activity stereoselectively hydrolyzing the ester portion of compound [1], a microorganism producible such the enzyme in a solution having pH suitable for the enzyme or its culture broth.

With progress of the reaction, pH value gradually become lower due to occurrence of an alkanoic acid such as acetic acid. Therefore, it is preferable to maintain suitable pH value by adding an acid-neutralizing agent, such as a suitable alkali, e.g. aqueous calcium carbonate, aqueous sodium hydroxide, aqueous sodium carbonate or aqueous ammonia.

In case of reacting a racemic compound [1] with an enzyme(s), after adjusting pH to 6–8 with a buffer solution such as phosphate buffer etc., the reaction is preferably carried out at the temperature 24–40° C., preferably 25–37° C. and in the concentration of the substrate (0.1–80% (v/v)).

The culture medium for cultivation of the microorganisms related to the present invention is not limited as long as the microorganisms can grow in the culture medium. For example, there are illustrated carbohydrates such as glucose, galactose or sucrose, alcohols such as glycerol, organic acids or their salts such as acetic acid, sodium acetate, citric acid, malic acid, maleic acid, fumaric acid or gluconic acid, or a mixture thereof as carbon source, inorganic nitrogen compounds such as ammonium sulfate, ammonium nitrate or ammonium phosphate, organic nitrogen compounds such as urea, peptone, casein, yeast extract, meat extract, corn steep liquor or a mixture thereof as nitrogen source. Further, inorganic salts such as phosphoric acid salt, magnesium salt, calcium salt, manganese salt, iron salt, zinc salt cooper salt, or if suitable, vitamins may be used.

The microorganisms related to the present invention can be cultivated as in the usual manner, for example at pH 6–9, preferably 6.5–7.51 at the temperature 20–40° C., preferably 25–37° C., and aerobically for 10–96 hours.

According to the present invention, the objective optically active compound can be obtained by 1) adding the substrate [1] in racemate to the culture medium prepared above, or 2) mixing cells of the microorganisms obtained by centrifugation etc., or the treated cells (disrupted cells or cell-free extract) or mixing an enzyme(s) immobilized by usual way with a buffer and then adding the substrate to the mixture.

The reaction is carried out preferably at 15–50° C. and preferably at pH 4–9. Concentration of the substrate in the reaction mixture is preferably 0.1–80% (v/v) and the substrate may be added at once in the initial stage or in several times.

The reaction is usually carried out under stirring or agitation, and the reaction is preferably completed in 1–120 hours, depending on the concentration of the substrate or amount of the microorganisms. With measurement of optical purity on an optically active compound, preferably with subjecting to gas chromatography, the end point nay be preferably determined.

Thus obtained optically active compounds [2] and [3] remaining in the reaction medium are recovered and purified by extraction of them with ethyl acetate and followed by distillation or subjecting to many kinds of chromatography. For example, after removal of cells of the microorganisms from the reaction medium by centrifugation, they are extracted with a solvent such as ethyl acetate. The extract is dried with anhydrous magnesium sulfate, and then the solvent is evaporated in vacuo to obtain a mixture of optically active compounds [2] and [3] in syrup.

Additionally, extraction, distillation, and many kinds of chromatography may be carried out.

According to the present invention, optical purity of an optically active compound [3] in which the ester portion is hydrolyzed is 25–80.5% ee. Therefore, after recovery of the compound with a solvent such as ethyl acetate, the compound is again esterified and by reacting said esterified compound (in racemate) with a microorganism which has the stereoselective activity reversed to the activity of a microorganism used in the first step, culture broth thereof or an enzyme(s) derived from the microorganism, there is obtainable each optical isomer (about 40–45% yield against racemate, each optical activity field; 80–90%). In this point the process of the present invention is efficient and economical.

The microorganisms used in the present invention are ones having the activity stereoselectively hydrolyzing the ester portion of a racemic 4-halogeno-3-alkanoyloxybutyronitrile, preferably following four strains. Furthermore, culture broth of these microorganisms and an enzyme(s) derived from these microorganisms can be also used.

Further, by using enzyme preparations having the activity stereoselectively hydrolyzing the ester portion of compound [1], optically active compounds [2] and [3] are also obtainable. That is, by reacting a compound [1] in racemate with an enzyme preparation having the activity selectively hydrolyzing the ester portion, such as a lipase preparation, there are obtainable optically active (R) compound [2] and (S) compound [3].

The following strains are preferably used in the present invention, and these strains were named DS-K-717 strain, DS-K-19 strain, DS-mk3 strain and DS-S-75 strain, respectively. These strains except DS-S-75 strain are newly isolated from the soil and are identified to strains belonging to species of the genus Pseudomonas from their physiological and bacteriological properties. These strains have been deposited on Mar. 12, 1996, with the National Institute of Bioscience and Human-Technology Agency of Industrial Science and Technology, Japan under Budapest Treaty with an accession number of FERM BP-7077, FERM BP-7076 and FERM BP-7078, respectively.

Physiological and bacteriological properties of DS-S-75 strain belonging to a species of the genus Enterobacter are described in European Patent Publication A 0745681, and said strain has been deposited with an accession number of FERM BP-5494 under Budapest Treaty.

Physiological and bacteriological properties on new strains (DS-K-717 strain, DS-K-19 strain and DS-mk3 strain) are shown below.

Growth in various media

1. Bouillon-agar plate medium (30° C., cultivation for 3 days)

| | Strains | DS-K-717 | DS-K-19 | DS-mk3 |
|---|---|---|---|---|
| a) | Speed of colony growth: | ordinary | ordinary | ordinary |
| b) | Shape of colonies: | circular | circular | circular |
| c) | Shape of colony surface: | smooth | smooth | smooth |
| d) | Raised condition of colonies: | convex | convex | convex |
| e) | Periphery of colonies: | entire | entire | entire |
| f) | Contents of colonies: | homogeneous | homogeneous | homogeneous |
| g) | Color of colonies: | white | white | pale yellow |
| h) | Transparency of colonies: | none | translucent | none |
| i) | Gloss of colonies: | yes | yes | yes |
| j) | Formation of soluble pigment: | none | none | none |

2. Bouillon-agar slant medium (30° C., cultivation for 3 days)

| | Strains | DS-K-717 | DS-K-19 | DS-mk3 |
|---|---|---|---|---|
| a) | Growth degree: | good | good | good |
| b) | Growth condition: | expansive | expansive | expansive |
| c) | Shape of colony surface: | smooth | smooth | smooth |
| d) | Shape of colony in section: | flat | flat | flat |
| e) | Gloss of colonies: | yes | yes | yes |
| f) | Color of colonies: | white | white | pale yellow |
| g) | Transparency of colonies: | none | translucent | none |

3. Bouillon-liquid medium (30° C., cultivation for 3 days)

| | Strains | DS-K-717 | DS-K-19 | DS-mk3 |
|---|---|---|---|---|
| a) | Growth degree: | good | good | good |
| b) | Generation of gas: | none | none | none |
| c) | Coloring of medium: | none | none | none |

4. Bouillon-gelatin stuck medium

| Strains | DS-K-717 | DS-K-19 | DS-mk3 |
|---|---|---|---|
| | not liquefied | not liquefied | liquefied |

5. Physiological properties

| | Strains | DS-K-717 | DS-K-19 | DS-mk3 |
|---|---|---|---|---|
| 1) | Reduction on nitrate | − | − | − |
| 2) | MR test | − | + | − |
| 3) | VP test | − | − | − |
| 4) | Production of indole | − | − | − |
| 5) | Production of $H_2S$ | − | − | − |
| 6) | Hydrolysis of starch | − | − | + |
| 7) | Denitrification | − | − | − |
| 8) | Utilization of citric acid | + | + | − |
| 9) | Utilization of inorganic nitrogen source | + | + | + |

-continued

| | | | | | | |
|---|---|---|---|---|---|---|
| 10) Production of fluorescent pigment | – | | – | | – | |
| 11) Urease | – | | – | | – | |
| 12) Oxidase | + | | + | | + | |
| 13) Catalase | – | | + | | – | |
| 14) pH range for growth | 5.5–8.5 | | 6–9.5 | | 5.5–9.5 | |
| 15) Reaction to oxygen | aerobic | | aerobic | | aerobic | |
| 16) O-F test | 0 | | 0 | | 0 | |
| 17) Accumulation of PHB | + | | + | | – | |
| 18) Decarboxylation of lysine | + | | + | | ± | |
| 19) Production of gas and acid from saccharides | | | | | | |

| | DS-K-717 | | DS-K-19 | | Ds-mk3 | |
|---|---|---|---|---|---|---|
| Strains | acid | gas | acid | gas | acid | gas |
| D-Glucose | + | – | + | – | ± | – |
| D-Galactose | + | – | + | – | + | – |
| Fluctose | + | – | + | – | + | – |
| Lactose | – | – | – | – | – | – |
| Glycerin | – | – | ± | – | + | – |
| Mannitol | – | – | – | – | – | – |

6. Morphological properties

| Strains | DS-K-717 | DS-K-19 | DS-mk3 |
|---|---|---|---|
| 1) Shape of cells | rods | rods | rods |
| 2) Size of cells ($\mu$m) | 1.6–3.2 | 1.8 | 1 |
| 3) Width of cells ($\mu$m) | 1–1.12 | 0.8 | 0.6 |
| 4) Pleomorphisms of cell | none | yes | none |
| 5) Flagella | single polar | single polar | single polar |
| 6) Mobility | + | + | + |
| 7) Gram stain | – | – | – |
| 8) Spores | – | – | – |
| 9) Acid fastness | – | – | – |
| 10) Capsules | none | none | none |
| 11) Metachromatic granules | none | none | none |

The present invention is illustratively explained by following examples, but should not be limited by these examples.

EXAMPLE 1

A nutrient medium (100 ml) consisting of polypeptone (1% w/v), east extract (1% w/v) and glycerin (1% w/v) having initial pH 7.0 were poured into a flask (500 ml) and the flask was sterilized under high pressure in vapor at 121° C., for 10 minuets in the usual manner and then, Pseudomonas sp. DS-mk3 were seeded and incubated by agitating at 120 rpm at 30° C. for 20 hours. The culture medium was adjusted to pH6.0 with 1N HCl and racemic 4-chloro-3-acetoxybutyronitrile was added in such that its concentration became 1% v/v. It was subject to reaction for 5 hours at 30° C. at 120 rpm. After completion of the reaction, ethyl acetate (100 ml) was added to extract optically active (R) 4-chloro-3-acetoxybutyronitrile (BAN) and (S) 4-chloro-3-hydroxybutyronitrile (a product that ester portion of the substrate was hydrolyzed) remaining in the reaction mixture. The recovery rate was 92% by weight. By analysis of the oil by subjecting to gas chromatography the oil contained 99% ee (R) 4-chloro-3-acetoxybutyronitrile (remaining rate 38% to racemic 4-chloro-3-acetoxybutyronitrile added) and 61% ee (S) 4-chloro-3-hydroxybutyronitrile (remaining rate 62% to racemic 4-chloro-3-acetoxybutyronitrile added).

Conditions on Gas Chromatography Analysis

Machine: Shimazu Seisakusho GC-14B

Capillary column: astec CHIRALDEX G-TA 30 m (inner diameter; 0.25 mm)

Analysis temperature: 120° C., Inject temp.: 200° C.

Carrier gas: nitrogen (flow 0.35 ml/min.), Split ratio: 1/100, Detection: FID 200° C.

Keeping time;

(S) 4-chloro-3-acetoxybutyronitrile: 30.0 min.

(R) 4-chloro-3-acetoxybutyronitrile: 35.3 min.

(S) 4-chloro-3-hydroxybutyronitrile: 38.4 min.

(R) 4-chloro-3-hydroxybutyronitrile: 40.2 min.

By using Pseudomonas sp. DS-K-717 or Pseudomonas sp. DS-K-19 as a microorganism for resolution and 4-chloro-3-acetoxybutyronitrile (BAN), 4-chloro-3-propionyloxybutyro-nitrile (BPN), 4-chloro-3-butylyloxybutyronitrile (BBN) or 4-chloro-3-isobutylyloxybutyronitrile (BisoBN) as a substrate resoluted, according to the method of Example 1, the reaction was carried out for 3–5 hours. Optically active substrate and optically active 4-chloro-3-hydroxybutyronitrile (BN) remaining in the reaction medium were analyzed.

[In case of using 4-chloro-3-acetoxybutyronitrile (BAN) as a substrate]

| Example | Bacteria | Remaining BAN (% ee) | Remaining rate (%) | Produced BN (% ee) | Production rate (%) |
|---|---|---|---|---|---|
| 2 | Pseudomonas sp. DS-K-717 | 99 (R) | 43 | 72 (S) | 57 |
| 3 | Pseudomonas sp. DS-K-19 | 99 (S) | 45 | 80.5 (R) | 55 |

[In case of using 4-chloro-3-propionyloxybutyronitrile (BPN) as a substrate]

| Example | Bacterium | Remaining BPN (% ee) | Remaining rate (%) | Produced BN (% ee) | Production rate (%) |
|---|---|---|---|---|---|
| 4 | Pseudomonas sp. DS-mk3 | 99 (R) | 19 | 28 (S) | 81 |

[In case of using 4-chloro-3-butylyloxybutyronitrile (BBN) as a substrate]

| Example | Bacteria | Remaining BBN (% ee) | Remaining rate (%) | Produced BN (% ee) | Production rate (%) |
|---|---|---|---|---|---|
| 5 | Pseudomonas sp. DS-K-19 | 99 (S) | 25.5 | 34.2 (R) | 74.5 |
| 6 | Pseudomonas sp. DS-mk3 | 99 (R) | 36 | 56.2 (S) | 63 |

[In case of using 4-chloro-3-isobutylyloxybutyronitrile (BisoBN) as a substrate]

| Example | Bacterium | Remaining BisoBN (% ee) | Remaining rate (%) | Produced BN (% ee) | Production rate (%) |
|---|---|---|---|---|---|
| 7 | Pseudomonas sp. DS-mk3 | 99 (R) | 15 | 34 (S) | 85 |

In the same manner as above, by using lipase powders instead of the microorganism, the good results were obtained as shown in the following Examples (8–13)

Reaction condition: substrate 1% v/v, phosphate buffer 50 mM, lipase powders: 1 g

[In case of using 4-chloro-3-acetoxybutyronitrile (BAN) as a substrate]

| Example | Enzyme | Remaining BAN (% ee) | Remaining rate (%) | Produced BN (% ee) | Production rate (%) |
|---|---|---|---|---|---|
| 8 | Lipase AK (Amano Seiyaku) | 99 (R) | 20.2 | 25.3 (S) | 79.8 |
| 9 | Lipase F-AP15 (Amano Seiyaku) | 99 (R) | 37.5 | 60.0 (S) | 62.5 |
| 10 | Lipase PS-D (Amano Seiyaku) | 99 (R) | 28.0 | 38.8 (S) | 72.0 |

[In case of using 4-chloro-3-butylyloxybutyronitrile (BAN) as a substrate]

| Example | Enzyme | Remaining BBN (% ee) | Remaining rate (%) | Produced BN (% ee) | Production rate (%) |
|---|---|---|---|---|---|
| 11 | Lipase AK (Amano Seiyaku) | 99 (R) | 24.5 | 34.2 (S) | 75.5 |
| 12 | Lipase F-AP15 (Amano Seiyaku) | 99 (R) | 26.3 | 35.7 (S) | 73.7 |
| 13 | Lipase PS-D (Amano Seiyaku) | 99 (R) | 23.3 | 30.3 (S) | 76.7 |

In the same manner as in Example 1 by using Enterobacter sp. DS-S-75 and four substrates, there were obtained following results.

| Example | Substrate | Remaining substrate (% ee) | Remaining rate (%) | Produced BN (% ee) | Production rate (%) |
|---|---|---|---|---|---|
| 14 | BAN | 99 (R) | 40.4 | 67 (S) | 59.6 |
| 15 | BPN | 99 (R) | 42.7 | 74 (S) | 57.3 |
| 16 | BisoBN | 99 (R) | 34.4 | 52 (S) | 65.6 |
| 17 | BBN | 99 (R) | 33.8 | 51 (S) | 66.2 |

Effect of the Present Invention

According to the process of the present invention, optically active 4-halogeno-3-hydroxybutyronitrile and its alkanoyl ester are conveniently and economically obtained.

What is claimed is:

1. A process for preparation of optically active compounds [2] and [3] represented by following formulae;

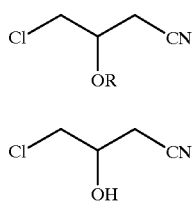

in which R means $C_2$–$C_4$ alkanoyl group;
which comprises reacting a racemic 4-halogeno-3-alkanoyloxybutyronitrile represented by following formula [1];

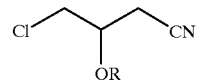

in which R is defined above;
with an intact microorganism, the culture broth thereof, or an enzyme(s) obtained from the microorganism which stereoselectively hydrolyzes the ester portion, and then recovering the optically active compounds [2] and [3], wherein the microorganism is a species of a genus selected from the group consisting of Pseudomonas and Enterobacter.

2. The process to claim 1 wherein the microorganism is a species of the genus Pseudomonas.

3. The process to claim 1 wherein the microorganism is a species of the genus Enterobacter.

4. The process to claim 1 for preparation of a (S) compound [2] and a (R) compound [3] by reacting a racemic compound [1] with the microorganism, the culture broth thereof, or an enzyme(s) obtained from the microorganism which stereoselectively hydrolyzes the ester portion of (R) form.

5. The process according to claim 1 for preparation of a (R) compound [2] and a (S) compound [3] by reacting a racemic compound [1] with the microorganism, the culture broth thereof; or an enzyme(s) obtained from the microorganism which stereoselectively hydrolyzes the ester portion of (S) form.

6. A process for preparation of optically active compounds [2] and [3] represented by following formulae;

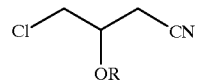
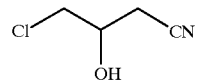

in which R means $C_2$–$C_4$ alkanoyl group;
which comprises reacting a racemic 4-halogeno-3-alkanoyloxybutyronitrile represented by following formula [1];

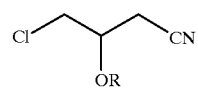

in which R is defined above;
with an intact microorganism, the culture broth thereof, or an enzyme(s) obtained from the microorganism which stereoselectively hydrolyzes the ester portion, and then recovering the optically active compounds [2] and [3], wherein the microorganism is selected from the group consisting of Pseudomonas sp. DS-K-19 (FERM BP-7076), Pseudomonas sp. DS-K-717 (FERM BP 7077), Pseudomonas sp. DS-mk3 (FERM BP-7078), and Enterobacter sp. DS-S-75 (FERM BP-5494).

7. The process according to claim 6 wherein the microorganism is Pseudomonas sp. DS-K-19 (FERM BP-7076).

8. The process according to claim 6 wherein the microorganism is Pseudomonas sp. DS-K-717 (FERM BP 7077).

9. The process according to claim 6 wherein the microorganism is Pseudomonas sp. DS-mk3 (FERM BP-7078).

10. The process according to claim 6 wherein the microorganism is Enterobacter sp. DS-S-75 (FERM BP-5494).

11. The process according to claim 6 for preparation of a (S) compound [2] and a (R) compound [3] by reacting a racemic compound [1] with the microorganism, the culture broth thereof, or an enzyme(s) obtained from the microorganism which stereoselectively hydrolyzes the ester portion of (R) form.

12. The process according to claim 6 for preparation of a (R) compound [2] and a (S) compound [3] by reacting a racemic compound [1] with the microorganism, the culture broth thereof, or an enzyme(s) obtained from the microorganism which stereoseletively hydrolyzes the ester portion of (S) form.

* * * * *